United States Patent [19]
Bouchard et al.

[11] Patent Number: 5,889,043
[45] Date of Patent: Mar. 30, 1999

[54] TAXOIDS, PREPARATION THEREOF AND PHARMACEUTICAL COMPOSITIONS CONTAINING SAME

[75] Inventors: Hervé Bouchard, Thiaia; Jean-Dominique Bourzat, Vincennes; Alain Commerçon, Vitry-sur-Seine, all of France

[73] Assignee: Rhone-Poulenc Rorer S.A., Antony, France

[21] Appl. No.: 913,972

[22] PCT Filed: Mar. 25, 1996

[86] PCT No.: PCT/FR96/00441

§ 371 Date: Sep. 26, 1997

§ 102(e) Date: Sep. 26, 1997

[87] PCT Pub. No.: WO96/30356

PCT Pub. Date: Oct. 3, 1996

[30] Foreign Application Priority Data

Mar. 27, 1995 [FR] France ..................................... 9503545
Dec. 22, 1995 [FR] France ..................................... 9515381

[51] Int. Cl.⁶ ........................ A61K 31/335; C07D 305/00
[52] U.S. Cl. ........................ 514/449; 549/510; 549/511
[58] Field of Search ..................................... 549/510, 511; 514/449

[56] References Cited

FOREIGN PATENT DOCUMENTS

0639577A1  2/1995  European Pat. Off. .
WO94/18164  8/1994  WIPO .

Primary Examiner—Amelia Owens
Attorney, Agent, or Firm—Finnegan, Henderson Farabow, Garrett & Dunner, L.L.P.

[57] ABSTRACT

The present invention relates to new taxoids of general formula:

in which:

Z represents a hydrogen atom or a radical of general formula:

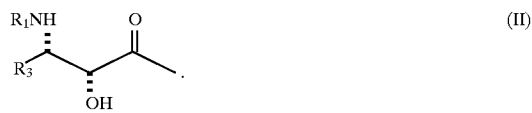

30 Claims, No Drawings

TAXOIDS, PREPARATION THEREOF AND PHARMACEUTICAL COMPOSITIONS CONTAINING SAME

The present invention relates to new taxoids of general formula:

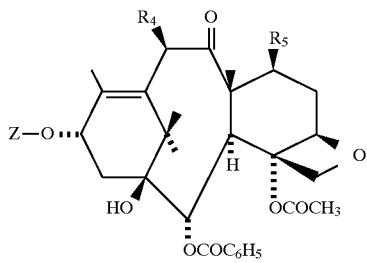

in which:

Z represents a hydrogen atom or a radical of general formula:

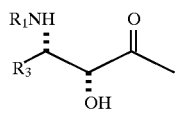

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals, $R_4$ represents an alkanoyloxy radical in which the alkanoyl portion contains 2 to 6 carbon atoms in an unbranched or branched chain, with the exception of an acetyl radical, an alkenoyloxy radical in which the alkenoyl portion contains 3 to 6 carbon atoms in an unbranched or branched chain or an alkynoyloxy radical in which the alkynoyl portion contains 3 to 6 carbon atoms in an unbranched or branched chain, these radicals being optionally substituted with one or more halogen atoms or with an alkoxy radical containing 1 to 4 carbon atoms or an alkylthio radical containing 1 to 4 carbon atoms or with a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur or nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a cycloalkanoyloxy radical in which the cycloalkanoyl portion contains 4 to 8 carbon atoms or a cycloalkenoyloxy radical in which the cycloalkenoyl portion contains 4 to 8 carbon atoms, or alternatively $R_4$ represents a benzoyloxy radical or a heterocyclic-carbonyloxy radical in which the heterocyclic portion represents a 5- or 6-membered aromatic heterocycle containing one or more hetero atoms chosen from oxygen, sulphur or nitrogen atoms, $R_5$ represents an alkoxy radical containing 1 to 6 atoms in an unbranched or branched chain, optionally substituted with an alkoxy radical containing 1 to 4 carbon atoms, an alkenyloxy radical containing 3 to 6 carbon atoms, an alkynyloxy radical containing 3 to 6 carbon atoms, a cycloalkyloxy radical containing 3 to 6 carbon atoms or a cycloalkenyloxy radical containing 3 to 6 carbon atoms, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur or nitrogen atoms, optionally substituted with an alkyl radical containing 1 to 4 carbon atoms or a phenyl radical or a phenylalkyl radical in which the alkyl portion contains 1 to 4 carbon atoms.

Preferably, the aryl radicals which can be represented by $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

Preferably, the radical $R_4$ represents an alkyloxyacetoxy radical in which the alkyl portion contains 1 to 4 carbon atoms, a cycloalkanoyloxy radical in which the cycloalkanoyl portion contains 4 to 8 carbon atoms, a cycloalkenoyloxy radical in which the cycloalkenoyl portion contains 4 to 8 carbon atoms, a benzoyloxy radical or a heterocyclic-carbonyloxy radical in which the heterocyclic portion represents a 5- or 6-membered aromatic heterocycle containing one or more hetero atoms chosen from oxygen, sulphur or nitrogen atoms, and $R_5$ represents an unbranched or branched alkoxy radical containing 1 to 6 carbon atoms, optionally substituted with a methoxy, ethoxy, methylthio, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl or N-piperidinocarbonyl radical.

More especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycarbonylamino) or trifluoromethyl radicals, or a 2- or 3-furyl, 2- or 3-thienyl or 2-, 4- or 5-thiazolyl radical, and $R_4$ represents an alkyloxyacetoxy radical in which the alkyl portion contains 1 to 4 carbon atoms, a cycloalkanoyloxy radical in which the cycloalkanoyl portion contains 4 to 6 carbon atoms or a pyridylcarbonyloxy radical, and $R_5$ represents an unbranched or branched alkyloxy radical containing 1 to 6 carbon atoms.

Still more especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, $R_4$ represents a methoxyacetoxy, cyclopropylcarbonyloxy, cyclopentylcarbonyloxy, 2-pyridylcarbonyloxy or 3-pyridylcarbonyloxy radical and $R_5$ represents a methoxy radical.

The products of general formula (I) in which Z represents a radical of general formula (II) display noteworthy antitumour and antileukaemic properties.

According to the present invention, the new products of general formula (I) in which Z represents a radical of general formula (II) may be obtained by esterification of a product of general formula:

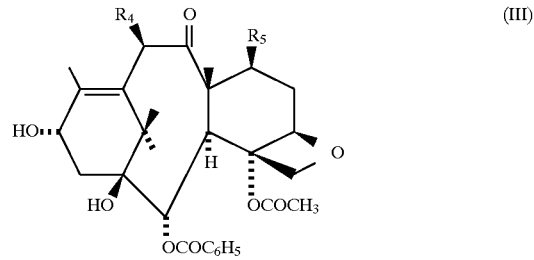

in which $R_4$ and $R_5$ are defined as above, by means of an acid of general formula:

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, or by means of a derivative of this acid, to obtain an ester of general formula:

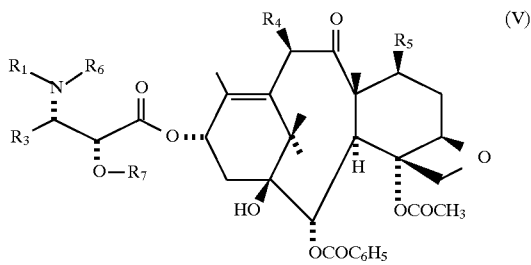

in which $R_1$, $R_3$, $R_4$, $R_5$, $R_6$ and $R_7$ are defined as above, followed by replacement of the protective groups represented by $R_7$ and/or $R_6$ and $R_7$ by hydrogen atoms.

The esterification by means of a product of general formula (XII) in which $X_1$ represents a hydroxyl radical may be performed in the presence of a condensing agent (carbodiimide, reactive carbonate) and an activating agent (aminopyridines) in an organic solvent (ether, ester, ketones, nitrites, aliphatic hydrocarbons, halogenated aliphatic hydrocarbons, aromatic hydrocarbons) at a temperature of between −10° and 90° C.

The esterification may also be carried out using a product of general formula (XII) in which $X_1$ represents a radical $R_4$—O—, working in the presence of an activating agent (aminopyridines) in an organic solvent (ethers, esters, ketones, nitrites, aliphatic hydrocarbons, halogenated aliphatic hydrocarbons, aromatic hydrocarbons) at a temperature of between 0° and 90° C.

The esterification may also be carried out using a product of general formula (XII) in which $X_1$ represents a halogen atom, in the presence of a base (tertiary aliphatic amine), working in an organic solvent (ethers, esters, ketones, nitriles, aliphatic hydrocarbons, halogenated aliphatic hydrocarbons, aromatic hydrocarbons) at a temperature of between 0° and 80° C.

Preferably, $R_6$ represents a hydrogen atom and $R_7$ represents a group protecting the hydroxyl function, or alternatively $R_6$ and $R_7$ together form a saturated 5- or 6-membered heterocycle.

When $R_6$ represents a hydrogen atom, $R_7$ preferably represents a methoxymethyl, 1-ethoxyethyl, benzyloxymethyl, trimethylsilyl, triethylsilyl, β-trimethylsilylethoxymethyl, benzyloxycarbonyl or tetrahydropyranyl radical.

When $R_6$ and $R_7$ together form a heterocycle, the latter is preferably an oxazolidine ring optionally monosubstituted or gem-disubstituted at position 2.

Replacement of the protective groups $R_7$ and/or $R_6$ and $R_7$ by hydrogen atoms may be performed, depending on their nature, in the following manner:

1) when $R_6$ represents a hydrogen atom and $R_7$ represents a group protecting the hydroxyl function, replacement of the protective groups by hydrogen atoms is performed by means of an inorganic acid (hydrochloric acid, sulphuric acid, hydrofluoric acid) or organic acid (acetic acid, methanesulphonic acid, trifluoromethanesulphonic acid, p-toluenesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of between −10° and 60° C., 2) when $R_6$ and $R_7$ together form a saturated 5- or 6-membered heterocycle, and more especially an oxazolidine ring of general formula:

in which $R_1$ is defined as above and $R_8$ and $R_9$, which may be identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$, together with the carbon atom to which they are linked, form a 4- to 7-membered ring, replacement of the protective group formed by $R_6$ and $R_7$ by hydrogen atoms may be performed, depending on the meanings of $R_1$, $R_8$ and $R_9$, in the following manner:

a) when $R_1$ represents a tert-butoxycarbonyl radical and $R_8$ and $R_9$, which may be identical or different, represent an alkyl radical or an aralkyl (benzyl) or aryl (phenyl) radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, treatment of the ester of general formula (V) with an inorganic or organic acid, where appropriate in an organic solvent such as an alcohol, yields the product of general formula:

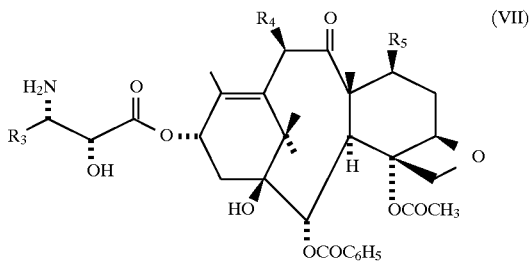

in which $R_3$, $R_4$ and $R_5$ are defined as above, which is acylated by means of benzoyl chloride in which the phenyl ring is optionally substituted or by means of thenoyl chloride, of furoyl chloride or of a product of general formula:

$$R_2\text{—O—CO—X} \quad (VIII)$$

in which $R_2$ is defined as above and X represents a halogen atom (fluorine, chlorine) or a residue —O—$R_2$ or —O—CO—O—$R_2$, to obtain a product of general formula (I) in which Z represents a radical of general formula (II).

Preferably, the product of general formula (V) is treated with formic acid at a temperature in the region of 20° C. to yield the product of general formula (VII).

Preferably, the acylation of the product of general formula (VII) by means of a benzoyl chloride in which the phenyl radical is optionally substituted or by means of thenoyl chloride, of furoyl chloride or of a product of general formula (VIII) is performed in an * inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is performed at a temperature of between 0° and 50° C., and preferably in the region of 20° C.

b) when $R_1$ represents an optionally substituted benzoyl radical, a thenoyl or furoyl radical or a radical $R_2O—CO—$ in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, replacement of the protective group formed by $R_6$ and $R_7$ by hydrogen atoms is performed in the presence of an inorganic acid (hydrochloric acid, sulphuric acid) or organic acid (acetic acid, methanesulphonic acid, trifluoromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of between −10° and 60° C., and preferably between 15° and 30° C.

According to the invention, the products of general formula (III), that is to say the products of general formula (I) in which Z represents a hydrogen atom and $R_4$ and $R_5$ are defined as above, may be obtained from 10-deacetylbaccatin III of formula:

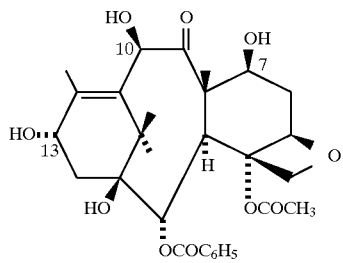
(IX)

It can be especially advantageous to protect the hydroxyl functions at the positions 7 and 13 selectively, for example in the form of a silyl diether which may be obtained by the action of a silyl halide of general formula:

$(R)_3—Si—Hal$      (X)

in which the symbols R, which may be identical or different, represent an alkyl radical containing 1 to 4 carbon atoms, optionally substituted with a phenyl radical, or a phenyl radical, on 10-deacetylbaccatin III, to obtain a product of general formula:

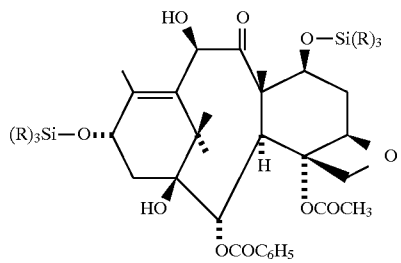
(XI)

in which R is defined as above, followed by the action of a product of general formula:

$R'_4—X_1$      (XII)

in which $R'_4$ is such that $R'_4—O—$ is identical to $R_4$ defined as above but cannot represent a hydrogen atom or a hydroxyl radical, and $X_1$ represents a halogen atom, to obtain a product of general formula:

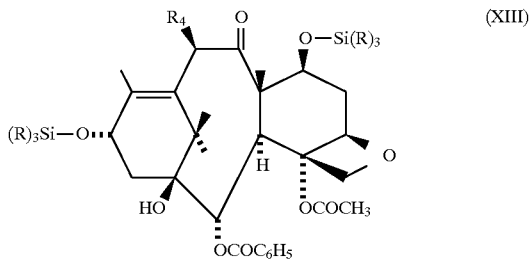
(XIII)

in which R and $R_4$ are defined as above, the silyl protective groups of which are replaced by hydrogen atoms to obtain a product of general formula:

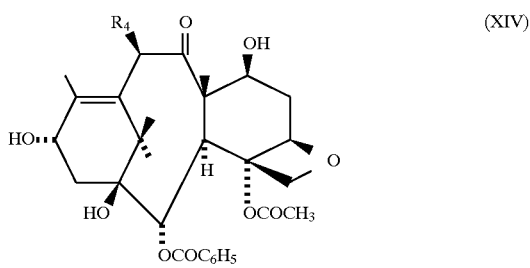
(XIV)

in which $R_4$ is defined as above, which is etherified selectively at position 7 by the action of a product of general formula:

$R'_5—X_2$      (XV)

in which $R'_5$ is such that $R'_5—O—$ is identical to $R_5$ defined as above and $X_2$ represents [lacuna] halogen atom or a sulphuric or sulphonic ester residue, to give the product of general formula (III).

Generally, the action of a silyl derivative of general formula (X) on 10-deacetylbaccatin III is performed in pyridine or triethylamine, where appropriate in the presence of an organic solvent such as an aromatic hydrocarbon, for instance benzene, toluene or xylenes, at a temperature between 0° C. and the refluxing temperature of the reaction mixture.

Generally, the action of a product of general formula (XII) on a product of general formula (XI) is performed, after metalation of the hydroxyl function at position 10 by means of an alkali metal hydride such as sodium hydride, an alkali metal amide such as lithium amide or an alkali metal alkylide such as butyllithium, working in an organic solvent such as dimethylformamide or tetrahydrofuran at a temperature of between 0° and 50° C.

Generally, the replacement of the silyl protective groups of the product of general formula (XIII) by hydrogen atoms is performed by means of an acid such as hydrofluoric acid or trifluoroacetic acid in the presence of a base such as triethylamine or pyridine optionally substituted with one or more alkyl radicals containing 1 to 4 carbon atoms, the base optionally being combined with an inert organic solvent such as a nitrile, for instance acetonitrile, or a halogenated aliphatic hydrocarbon such as dichloromethane at a temperature of between 0° and 80° C.

Generally, the action of a product of general formula (XV) on a product of general formula (XIV) is performed under the conditions described above for the action of a product of general formula (XII) on a product of general formula (XI).

According to the invention, the products of general formula (I) in which Z represents a radical of general formula (II), and $R_4$ and $R_5$ are defined as above may be obtained from a product of general formula:

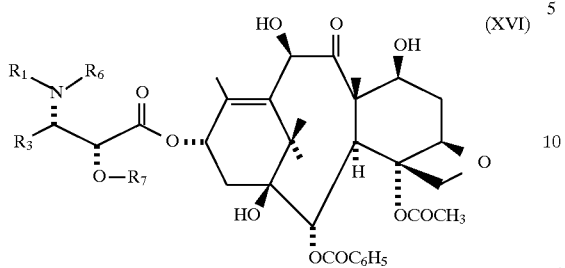

in which $R_1$, $R_3$, $R_6$ and $R_7$ are defined as above, by silylation at position 7 by means of a product of general formula (X), to obtain a product of general formula:

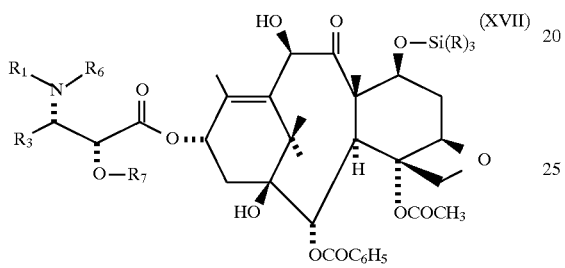

in which R, $R_1$, $R_3$, $R_6$ and $R_7$ are defined as above, which is functionalized at position 10 by means of a product of general formula (XII) to give a product of general formula:

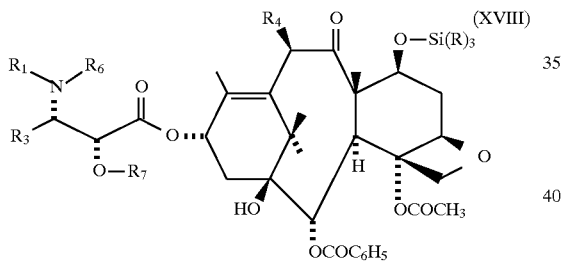

in which R, $R_1$, $R_3$, $R_4$, $R_6$ and $R_7$ are defined as above, the silyl protective group of which is replaced by a hydrogen atom to give a product of general formula:

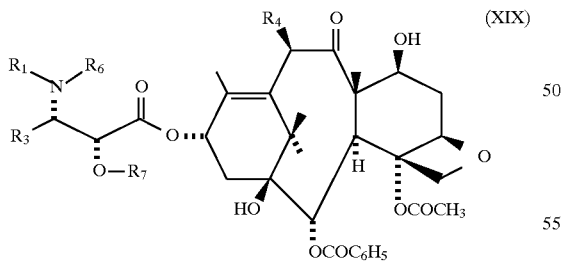

which, by the action of a product of general formula (XV), yields the product of general formula (V), the protective groups of which are replaced by hydrogen atoms to give a product of general formula (I) in which Z represents a radical of general formula (II).

The reactions used for silylation, 10 functionalization and replacement of the protective groups by hydrogen atoms are performed under conditions similar to those described above.

The products of general formula (XVI) may be obtained under the conditions described in European Patent EP 0,336, 841 and International Applications PCT WO 92/09589 and WO 94/07878, or from the products of general formula:

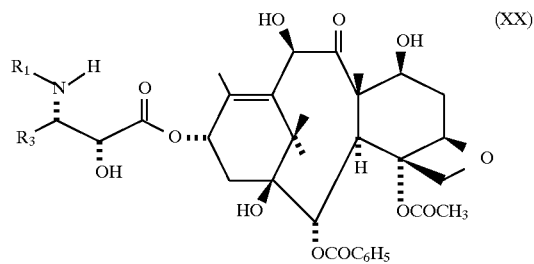

in which $R_1$ and $R_3$ are defined as above, according to known methods for protecting the hydroxyl function of the side chain without affecting the remainder of the molecule.

According to the invention, the products of general formula (I) in which Z represents a hydrogen atom or a radical of general formula (II) may be obtained by the action of activated Raney nickel, in the presence of an aliphatic alcohol containing 1 to 3 carbon atoms, on a product of general formula:

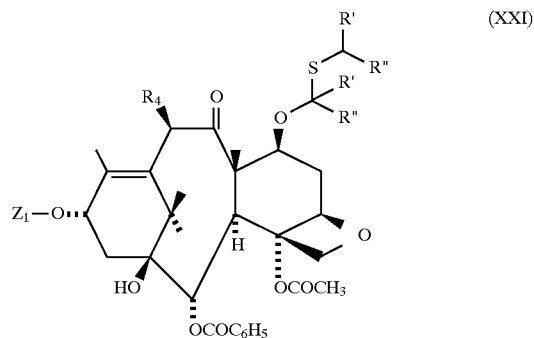

in which $R_4$ is defined as above and R' and R", which may be identical or different, represent a hydrogen atom an alkyl radical containing 1 to 6 carbon atoms, an alkenyl radical containing 2 to 6 carbon atoms, an alkynyl radical containing 2 to 6 carbon atoms, a cycloalkyl radical containing 3 to 6 carbon atoms or a cycloalkenyl radical containing 3 to 6 carbon atoms, or alternatively R' and R", together with the carbon atom to which they are linked, form a cycloakyl radical containing 3 to 6 carbon atoms or a cycloalkenyl radical containing 4 to 6 carbon atoms, and $Z_1$ represents a hydrogen atom or a radical of general formula:

in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, and $R_4$ is defined as above, to obtain a product of general formula:

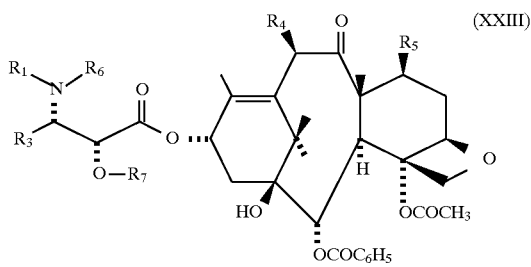

(XXIII)

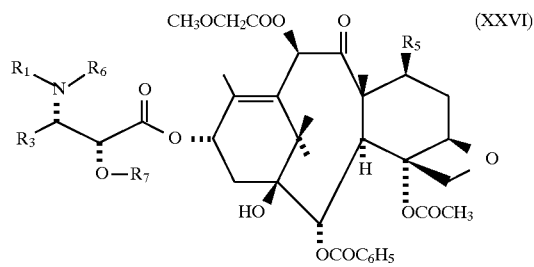

(XXVI)

followed, when $Z_1$ represents a radical of general formula (XXII), that is to say when the product of general formula (XXIII) is identical to the product of general formula (V), by replacement of the protective groups represented by $R_6$ and/or $R_6$ and $R_7$ by hydrogen atoms under the conditions described above.

Generally, the action of activated Raney nickel in the presence of the aliphatic alcohol is performed at a temperature of between −10° and 60° C.

According to the invention, the product of general formula (XXI) in which $Z_1$ and $R_4$ are defined as above may be obtained by the action of a dialkyl sulphoxide of general formula:

(XXIV)

in which R' and R" are defined as above, on a product of general formula (XIX).

Generally, the reaction of the sulphoxide of general formula (XXIV), preferably dimethyl sulphoxide, with the product of general formula (XIX) is performed in the presence of a mixture of acetic acid and acetic anhydride or a derivative of acetic acid such as a haloacetic acid at a temperature of between 0° and 50° C., and preferably in the region of 25° C.

According to the invention, the products of general formula (I) in which Z represents a radical of general formula (II) may be obtained by the action of a product of general formula (XII) on a product of general formula:

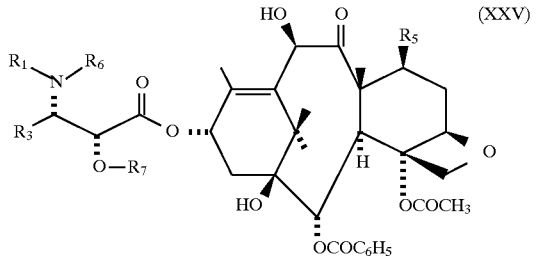

(XXV)

in which $R_1$, $R_3$, $R_5$, $R_6$ and $R_7$ are defined as above, working under the conditions described for the action of a product of general formula (XII) on a product of general formula (XI), followed by replacement of the protective groups represented by $R_7$ or $R_6$ and $R_7$ by hydrogen atoms under the conditions described above.

The product of general formula (XXV) may be obtained by the action of a zinc halide such as zinc iodide or hydrazine on a product of general formula:

in which $R_1$, $R_3$, $R_5$, $R_6$ and $R_7$ are defined as above.

Generally, the reaction is performed working in an aliphatic alcohol containing 1 to 4 carbon atoms, such as methanol or ethanol, at a temperature of between 0° and 50° C.

The product of general formula (XXVI) may be obtained by the action of activated Raney nickel in the presence of an aliphatic alcohol containing 1 to 3 carbon atoms on a product of general formula:

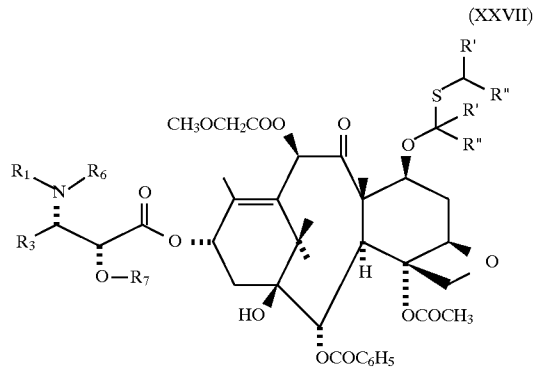

(XXVII)

in which $R_1$, $R_3$, $R_6$, $R_7$, R' and R" are defined as above, working under the conditions described above for the preparation of a product of general formula (I) from a product of general formula (XXI).

The product of general formula (XXVII) may be obtained by the action of a sulphoxide of general formula (XXIV) on a product of general formula:

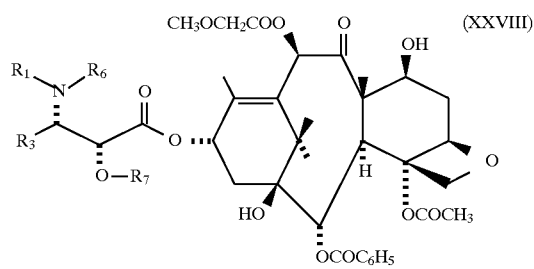

(XXVIII)

in which $R_1$, $R_3$, $R_6$ and $R_7$ are defined as above, working under the conditions described above for the action of a sulphoxide of general formula (XXIV) on a product of general formula (XIX).

The product of general formula (XXVIII) may be obtained from a product of general formula:

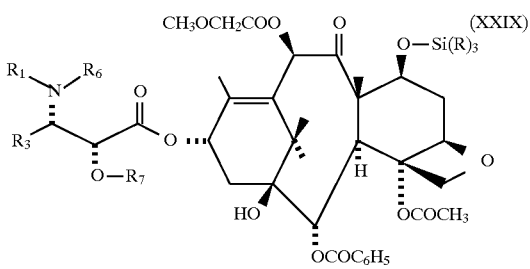

(XXIX)

in which $R_1$, $R_3$, $R_6$ and $R_7$ are defined as above, working under the conditions described above for replacing the sylil groups of the product of general formula (XIII) by hydrogen atoms.

The product of general formula (XXIX) may be prepared under the conditions described in International Application PCT WO 95/11241.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M.L. Shelanski et al., Proc. Natl. Acad. Sci. USA, 70, 765–768 (1973). Study of the depolymerization of microtubules to tubulin is performed according to the method of G. Chauvière t al., C.R. Acad. Sci., 293, series II, 501–503 (1981). In this study, the products of general formula (I) in which Z represents a radical of general formula (II) were shown to be at least as active as taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The examples which follow illustrate the present invention.

EXAMPLE 1

243 mg of 4α-acetoxy-2α-benzoyloxy-5α,20 -epoxy-1β-hydroxy-7β-methoxy-9-oxo-10β-(3-pyridylcarbonyl)oxy-11-taxen-13α-yl (2R,4S,5R)-3-tert-butoxycarbonyl-2-(4-methoxyphenyl)-4-phenyl-1,3-oxazolidine-5-carboxylate are dissolved in 4.5 cm³ of a 0.1N ethanolic solution of hydrochloric acid containing 1% of water. The solution thereby obtained is stirred for 3 hours at a temperature in the region of 20° C. and 25 cm³ of dichloromethane are then added. The organic phase is separated after settling has taken place and washed successively two times with cm³ of saturated aqueous sodium hydrogen carbonate solution, dried over magnesium sulphate, filtered and concentrated to dryness under reduced pressure (2.7 kPa) at 40° C. 290 mg of a white foam are obtained, which is purified by chromatography on silica gel deposited on plates [(gel thickness 1 mm, plates 20×20 cm, eluent: dichloromethane/methanol (95:5 by volume)] in 80-mg fractions (4 plates). After localization with UV rays of the zone corresponding to the adsorbed product sought, this zone is scraped off and the silica collected is washed on sintered glass with ten times cm³ of ethyl acetate. The filtrates are combined and concentrated to dryness under reduced pressure (2.7 kPa) at 20° C. A white foam is obtained, which is repurified according to the same technique [(2 plates: 20×20×1 mm; eluent: dichloromethane/methanol (95:5 by volume)]. 132 mg of 4α-acetoxy-2α-benzoyloxy-5β,20-epoxy-1β-hydroxy-7β-methoxy-9-oxo-10β-(3-pyridylcarbonyl)oxy-11-taxen-13α-yl (2R,3S)-3-tert-butoxycarbonylamino-2-hydroxy-3-phenylpropionate are thereby obtained in the form of a white foam, the characteristics of which are as follows:

optical rotation: $[\alpha]_{20}^D = -34$ (c=0.5; methanol).

$^1$H NMR spectrum (300 MHz; CDCl$_3$: chemical shifts δ in ppm; coupling constants J in Hz): 1.30 (s, 3H: —CH$_3$ at position 16 or 17); 1.35 [(s, 12H: —C(CH$_3$)$_3$ and —CH$_3$ at position 16 or 17]; 1.75 (s, 3H: —CH$_3$); 1.82 and 2.77 (2 mts, 1H each: —CH$_2$— at position 6); 1.97 (s, 3H: —CH$_3$); 2.35 (d, J=9, 2H: —CH$_2$— at position 14); 2.39 (s, 3H: —COCH$_3$); 3.38 (d, J=5, 1H: —OH at position 2'); 3.42 (s, 3H: —OCH$_3$); 3.88 (d, J=7.5, 1H: —H at position 3); 3.96 (dd, J=11 and 7.5, 1H: —H at position 7); 4.18 and 4.32 (2d, J=8.5, 1H each: —CH$_2$— at position 20); 4.64 (mt, 1H: —H at position 2'); 4.98 (broad d, J=10, 1H: —H at position 5); 5.28 (broad d, J=10, 1H: —H at position 3'); 5.39 (d, J=10, 1H: —CONH—); 5.70 (d, J=7.5, 1H: —H at position 2); 6.22 (broad, J=9, 1H: -H at position 13); 6.69 (s, 1H: —H at position 10); from 7.25 to 7.45 (mt, 5H: —C$_6$H$_5$ at position 3'); 7.44 [(dd, J=8.5 and 6, 1H: —OCOC$_5$H$_4$N (—H at position 5)]; 7.50 [(dd, J=7.5, 2H: —OCOC$_6$H$_5$ (—H at position 3 and H at position 5)]; 7.62 [(t, J=7.5, 1H: —OCOC$_6$H$_5$(—H at position 4)]; 8.12 [(d, J=7.5, 2H: —OCOC$_6$H$_5$(—H at position 2 and —H at position 6)]; 8.35 [(dt, J=8.5 and 1, 1H: —OCOC$_5$H$_4$N(—H at position 4)]; 8.82 (dd, J=6 and 1, 1H: -OCOC$_5$H$_4$N(—H at position 6)]; 9.32 (d, J=1, 1H: —OCOC$_5$H$_4$N(-H at position 2)].

4α-Acetoxy-2α-benzoyloxy-5β,20-epoxy-1β-hydroxy-7β-methoxy-9-oxo-10β-(3-pyridylcarbonyl)oxy-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

290 mg of 4α-acetoxy-2α-benzoyloxy-5β,20-epoxy-1β,10β-dihydroxy-7β-methoxy-9-oxo-11-taxen-13α-yl (2R,4S,5R)-3-tert-butyoxycarbonyl-2-(4-methoxyphenyl)-4-phenyl-1,3-oxazolidine-5-carboxylate, 18.5 mg of 4-(dimethylamino)pyridine, 0.5 g of 4 Å molecular sieve and 112 mg of N,N'-dicyclohexylcarbodiimide are added at a temperature in the region of 20° C. to a solution, kept stirring under an argon atmosphere, of 46 mg of 3-pyridinecarboxylic acid in 25 cm³ of anhydrous ethyl acetate. The reaction mixture is kept stirring for 16 hours at a temperature in the region of 20° C., 46 mg of 2-pyridinecarboxylic acid, 18.5 mg of 4-(dimethylamino) pyridine, 0.5 g of 4 Å molecular sieve and 112 mg of N,N'-dicyclohexylcarbodiimide are then added and the mixture is again kept stirring for 24 hours, this cycle then being repeated twice more. The reaction mixture is filtered through sintered glass lined with Celite. The sintered glass is washed with 2 times 50 cm³ of ethyl acetate, and the filtrates are combined, washed successively 2 times with cm³ of saturated aqueous sodium hydrogen carbonate solution and 6 times with cm³ of distilled water, dried over magnesium sulphate, filtered and concentrated to dryness under reduced pressure (2.7 kPa) at 40° C. 298 mg of 4α-acetoxy-2α-benzoyloxy-5β,20-epoxy-1β-hydroxy-7β-methoxy-9-oxo-10β-(3-pyridylcarbonyl)oxy-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-Acetoxy-2α-benzoyloxy-5β,20-epoxy-1β,10β-dihydroxy-7β-methoxy-9-oxo-11-tazen-13α-yl (2R,4S,5R)-3-tert-butoxycarbonyl-2-(4-methoxyphenyl)-4-phenyl-1,3-oxazolidine-5-carboxylate may be prepared in the following manner 0.263 cm³ of hydrazine monohydrate is added dropwise and at a temperature in the region of 20° C. to a solution, kept stirring under an argon atmosphere, of 150 mg of 4α-acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 4 cm³ of anhydrous ethanol. The reaction medium is kept stirring for 1 hour at a temperature in the region of 20° C. and then poured into a mixture of 100 cm³ of ethyl acetate and 50 cm³ of distilled water. The organic phase is separated after settling has taken place and the aqueous phase is re-extracted 2 times with 50 cm³ of ethyl acetate. The organic phases are combined, washed 4 times with 50 cm³ of distilled water, dried over magnesium sulphate, filtered and concentrated to dryness under reduced pressure (2.7 kPa) at 40° C. 180 mg of a white foam are obtained, which is purified by chromatography on silica gel deposited on plates [(gel thickness 1 mm, plates 20×20 cm, eluent: dichloromethane/methanol (90:10 by volume)] in 90 mg fractions (2 plates). After localization with UV rays of the zone corresponding to the adsorbed product sought, this zone is scraped off and the silica collected is washed on sintered glass 10 times with 10 cm³ of ethyl acetate. The filtrates are combined and concentrated to dryness under reduced pressure (2.7 kPa) at 40° C. 113 mg of 4α-acetoxy-2α-benzoyloxy-5β,20-epoxy-1β,10β-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-Acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)4-phenyl-1,3-oxazolidine-5-carboxylate may be prepared in the following manner:

100 cm³ of an ethanolic suspension of activated nickel prepared by Raney's method (obtained from 80 cm³ of the approximately 50% commercial aqueous suspension, by successive washing to a pH in the region 150 cm³ of ethanol) are added at a temperature in the region of 20° C. to a solution, kept stirring under an argon atmosphere, of 1.041 g of 4α-acetoxy-2α-benzoyloxy-5β,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-1,3-oxazolidine-5-carboxylate in 100 cm³ of anhydrous ethanol. The reaction mixture is kept stirring for 7 days at a temperature in the region of 20° C. and is then filtered through sintered glass. The sintered glass is washed 3 times with 100 cm³ of ethanol and the filtrates are combined and concentrated to dryness under reduced pressure (2.7 kPa) at 40° C. 821 mg of a white foam are obtained, which is purified by chromatography on 75 g of silica (0.063-0.2 mm) contained in a column 2.5 cm in diameter [eluent: dichloromethane/ethyl acetate (90:10 by volume)], collecting 5-cm³ fractions. The fractions containing only the product sought are pooled and concentrated to dryness under reduced pressure (2.7 kPa) at 40° C. 228 mg of 4α-acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-Acetoxy-2β-benzoyloxy-5β,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

3.35 cm³ of acetic acid and 11.5 cm³ of acetic anhydride are added at a temperature in the region of 20° C. to a solution, kept stirring under an argon atmosphere, of 5 g of 4α-acetoxy-2β-benzoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 165 cm³ of anhydrous dimethyl sulphoxide. The reaction mixture is kept stirring for 3 days at a temperature in the region of 20° C. and is then poured into 500 cm³ of dichloromethane. 100 cm³ of saturated aqueous potassium carbonate solution are then added with efficient stirring to a pH in the region of 7. After stirring for 10 minutes, the organic phase is separated after settling has taken place and the aqueous phase is re-extracted 2 times with 250 cm³ of dichloromethane. The organic phases are combined, washed 3 times with 100 cm³ of distilled water, dried over magnesium sulphate, filtered and concentrated to dryness under reduced pressure (2.7 kPa) at 40° C. 9.5 g of a pale yellow oil are obtained, which is purified by chromatography on 250 g of silica (0.063–0.4 mm) contained in a column 3 cm in diameter [eluent:

dichloromethane/methanol (99:1 by volume)], collecting 50 cm³ fractions. The fractions containing only the product sought are pooled and concentrated to dryness under reduced pressure (2.7 kPa) at 40° C. 3.01 g of 4α-acetoxy-2β-benzoyloxy-5β,20-epoxy-1β-hydroxy-10β-methoxyacetoxy-7β-methylthiomethoxy-9-oxo-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-Acetoxy-2β-benxoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

220 cm³ of triethylamine/hydrofluoric acid (mole ratio 1:3) complex are added dropwise at a temperature in the region of 0° C. to a solution, kept stirring under an argon atmosphere, of 20 g of 4α-acetoxy-2α-benzoyloxy-5β,20-epoxy-7β-triethylsilyloxy-1β-hydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate in 200 cm³ of anhydrous dichloromethane. The reaction mixture is then warmed to a temperature in the region of 20° C., maintained for 3 hours at this temperature and poured into 4 litres of saturated aqueous sodium hydrogen carbonate solution. The pH of the reaction medium thus being brought to around 7. After stirring for 10 minutes, the organic phase is separated after settling has taken place and the aqueous phase is extracted 2 times with 100 cm³ of dichloromethane. The organic phases are combined, washed with 100 cm³ of distilled water, dried over magnesium sulphate, filtered and concentrated to dryness under reduced pressure (2.7 kPa) at 40° C.

17.4 g of 4α-acetoxy-2α-benzoyloxy-5β,20-epoxy-1β,7β-dihydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a white foam.

4α-Acetoxy-2α-benzoyloxy-5β,20-epoxy-7β-triethylsilyloxy-1β-hydroxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate may be prepared under the conditions described in International Application PCT WO 95/11241.

EXAMPLE 2

Working as in Example 1, but starting from 210 mg of 4α-acetoxy-2α-benzoyloxy-5β,20-epoxy-1β-hydroxy-7β-methoxy-9-oxo-10β-(2-pyridylcarbonyl)oxy-11-taxen-13α-yl (2R,4S,5R)-3-tert-butoxycarbonyl-2-(4-methoxyphenyl)-4-phenyl-1,3-oxazolidine-5-carboxylate, 145 mg of 4α-acetoxy-2α-benzoyloxy-5β,20-epoxy-1β-hydroxy-7β-methoxy-9-oxo-10β-(2-pyridylcarbonyl)oxy-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D = -52$ (c=0.5; methanol).

$^1$H NMR spectrum (400 MHz: CDCl$_3$); chemical shifts δ in pp,; coupling constants J in Hz): 1.31 (s, 3H: —CH$_3$ at postion 16 or 17); 1.37 [(s, 12H: —C(CH$_3$)$_3$ and —CH$_3$ at position 16 or 17]; 1.74 (8, 1H: —OH at position 1); 1.78 (s, 3H: —CH$_3$); 1.82 and 2.78 (2 mts, 1H each: —CH$_2$— at position 6); 1.97 (s, 3H: —CH$_3$); 2.35 (d, J=9, 2H:
—CH$_2$— at position 14); 2.40 (s, 3H: —COCH$_3$); 3.40 (d, J=4.5, 1H: —OH at position 2'); 3.43 (s, 3H: —OCH$_3$); 3.92 (d, J=7.5, 1H: —H at position 3); 3.98 (dd, J=11 and 7, 1H: —H at position 7); 4.20 and 4.32 (2 d, J=8.5, 1H each: —CH$_2$— at position 20); 4.64 (mt, 1H: —H at position 2'); 5.00 (broad d, J=10, 1H: —H at position 5); 5.28 (broad d, J=10, 1H: —H at position 3'); 5.43 (d, J=10, 1H: —CONH—); 5.73 (d, J=7.5, 1H: —H at position 2); 6.22 (broad t, J=9, 1H: —H at 13); 6.67 (8, 1H: -H at position 10); from 7.25 to 7.45 (mt, 5H: —C$_6$H$_5$ at position 3'); 7.51 [(mt, 3H:
—OCOC$_6$H$_5$(—H at position 3 and H at position 5) and —OCOC$_5$H$_4$N(—H at position 5)]; 7.61 [(t, J=7.5, 1H: —OCOC$_6$H$_5$(—H at position 4)]; 7.88 [(split t, J=8 and 1, 1H:. —OCOC$_5$H$_4$N(—H at position 4)]; 8.12 [(d, J=7.5, 2H: —OCOC$_6$H$_5$(—H at position 2 and —H at position 6)]; 8.20 (broad d, J=8, 1H: —OCOC$_5$H$_4$N(—H at position 3)); 8.82 (broad dd J=5 and 1, 1H: —OCOC$_5$H$_4$N (—H at position 6)].

Working as in Example 1, but starting from 300 mg of 4α-acetoxy-2α-benzoyloxy-5β,20-epoxy-1β,10β-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate, 230 mg of 4α-acetoxy-2α-benzoyloxy-5β,20-epoxy-1β-hydroxy-7β-methoxy-9-oxo-10β-(2-pyridylcarbonyl)oxy-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

EXAMPLE 3

Working as in Example 1, but starting from 300 mg of 4α-acetoxy-2a-benzoyloxy-10β-cyclopentylcarbonyloxy-5β,20-epoxy-1β-hydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate, 96 mg of 4α-acetoxy-2α-benzoyloxy-10β-cyclopentylcarbonyloxy-5β,20-epoxy-1β-hydroxy-7β-methoxy-9-oxo-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D = -66$ (c=0.5; methanol).

$^1$H NMR spectrum (400 MHz; CDCl$_3$; chemical shifts δ in ppm; coupling constants J in Hz); 1.25 (s, 6H: —CH$_3$ at positions 16 and 17); 1.39 [s, 9H; —C(CH$_3$)$_3$]; from 1.55 to 1.80 and from 1.90 to 2.10 (2 mts, 4H each: —CH$_2$— of the cyclopentyl); 1.71 (s, 1H: —OH at position 1); 1.75 (s, 3H: —CH$_3$); 1.82 and 2.75 (2 mts, 1H each: —CH$_2$— at position 6); 1.93 (s, 3H: —CH$_3$); 2.33 (d, J=9 Hz, 2H: —CH$_2$— at position 14); 2.39 (s, 3H: —COCH$_3$); 2.95 (mt, 1H:=CH— of the cyclopentyl); 3.38 (s, 3H: —OCH$_3$); 3.40 (d, J=5, 1H: —OH at position 2'); 3.88 (d, J=7.5, 1H: —H at position 3); 3.91 (dd, J=11 and 7.5, 1H: —H at position 7); 4.19 and 4.32 (2 d, J=8.5, 1H each:
—CH$_2$ at position 20); 4.65 (mt, 1H: —H at position 2'); 4.98 (broad d, J=10, 1H: —H at position 5); 5.28 (broad d, J=10, 1H: —H at position 3'); 5.41 (d, J=10, 1H: —CONH—); 5.68 (d, J=7.5, 1H: —H at position 2); 6.21 (broad t, J=9, 1H: —H at position 13); 6.45 (s, 1H: —H at position 10); from 7.25 to 7.45 (mt, 5H:
—C$_6$H$_5$ at position 3'); 7.51 [t, J=7.5, 2H: —OCOC$_6$H$_5$ (—H at position 3 and H at position 5)]; 7.63 [t, J=7.5, 1H: —OCOC$_6$H$_5$ (—H at position 4)]; 8.12 [d, J=7.5, 2H: —OCOC$_6$H$_5$ (—H at position 2 and —H at position 6)].

Working as in Example 1, but starting from 300 mg of 4α-acetoxy-2α-benzoyloxy-5β,20-epoxy-1β,10β-dihydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate, 410 mg of 4α-acetoxy-2α-benzoyloxy-10β-cyclopentylcarbonyloxy-5β,20-epoxy-1β-hydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

EXAMPLE 4

Working as in Example 1, but starting from 300 mg of 4α-acetoxy-2β-benzoyloxy-10β-cyclopropyl-carbonyloxy-5β,20-epoxy-1β-hydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate, 130 mg of 4α-acetoxy-2α-benzoyloxy-10β-cyclopropylcarbonyloxy-5β,20-epoxy-1β-hydroxy-7β-methoxy-9-oxo-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D = -71$ (c=0.5; methanol).

$^1$H NMR spectrum (400 MHz; CDCl$_3$, chemical shifts δ in ppm; coupling constants J in Hz): 1.00 and 1.19 (2 mts, 2H each: —CH$_2$— of the cyclopropyl); 1.25 (s, 3H: —CH$_3$ at position 16 or 17); 1.27 (s, 3H: —CH$_3$ at position 16 or 17; 1.39 [s, 9H: —C(CH$_3$)$_3$]; 1.71 (s, 1H: —OH at position 1); 1.75 (s, 3H: —CH$_3$); from 1.70 to 1.90 (mt, 1H: =CH— of the cyclopropyl); 1.82 and 2.75 (2 mts, 1H each: —CH$_2$— at position 6); 1.93 (s, 3H: —CH$_3$); 2.33 (d, J=9, 2H: —CH$_2$— at position 14); 2.40 (s, 3H: —COCH$_3$); 3.35 (s, 3H: —OCH$_3$); 3.40 (d, J=5, 1H: —OH at position 2'); 3.88 (d, J=7.5, 1H: —H at position 3); 3.89 (dd, J=11 and 7.5, 1H: —H at position 7); 4.19 and 4.32 (2 d, J=8.5, 1H each: —CH$_2$— at position 20); 4.65 (mt, 1H: —H at position 2'); 5.00 (broad d, J=10, 1H: —H at position 5); 5.28 (broad d, J=10, 1H: —H at position 3'); 5.42 (d, J=10, 1H: —CON H—); 5.68 (d, J=7.5, 1H: —H at position 2); 6.21 (broad t, J=9, 1H: —H at position 13); 6.48 (s, 1H: —H at position 10);

from 7.25 to 7.45 (mt, 5H: —C$_6$H$_5$ at position 3'); 7.52 [t, J=7.5, 2H: —OCOC$_6$H$_5$ (—H at position 3 and H at position 5)]; 7.64 [t, J=7.5, 1H: —OCOC$_6$H$_5$ (—H at position 4)]; 8.12 [d, J=7.5, 2H: —OCOC$_6$H$_5$ (—H at position 2 and —H at position 6)].

Working as in Example 1, but starting from 300 mg of 4α-acetoxy-2α-benzoyloxy-5β,20-epoxy-1β,10β-dihydroxy-7β-methoxy-9-oxo-11-taxen-13a-yl (2R,4S,5R)-3-tert-butoxycarbonyl-2-(4-methoxyphenyl)-4-phenyl-1,3-oxazolidine-5-carboxylate, 435 mg of 4α-acetoxy-2α-benzoyloxy-10β-cyclopropylcarbonyloxy-5β,20-epoxy-1β-hydroxy-7β-methoxy-9-oxo-11-taxen-13α-yl (2R,4S,5R)-3-tert-butoxycarbonyl-2-(4-methoxyphenyl)-4-phenyl-1,3-oxazolidine-5-carboxylate are obtained in the form of a white foam.

EXAMPLE 5

Working as in Example 1, but starting from 430 mg of 4α-acetoxy-2α-benzoyloxy-5β,20-epoxy-1β-hydroxy-7β-methoxy-10β-methoxyacetoxy-9-oxo-11-taxen-13α-yl (2R,4S,5R)-3-tert-butoxycarbonyl-2-(4-methoxyphenyl)-4-phenyl-1,3-oxazolidine-5-carboxylate, 164 mg of 4α-acetoxy-2α-benzoyloxy-5β,20-epoxy-1β-hydroxy-7β-methoxy-10β-methoxyacetoxy-9-oxo-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_{20}^D$=−48 (c=0.5; methanol)

$^1$H NMR spectrum (300 MHz: CDCl$_3$; δ in ppm; coupling constants J in Hz): 1.17 (s, 3H: —H$_3$); 1.22 (a, 3H: —CH$_3$); 1.35 (s, 9H: —C(CH$_3$)$_3$); 1.75 (s, 3H: —CH$_3$); 1.80 and 2.75 (2 mts, 1H each: —CH$_2$— 6); 1.90 (s, 3H: —CH$_3$); 2.30 (d, J=9, 2H: —CH$_2$— 14); 2.37 (s, 3H: —COCH$_3$); 3.35 and 3.55 (2 s, 3H each: —OCH$_3$); 3.40 (d, J=5, 1H: —OH 2'); 3.85 (d, J=7, 1H: —H 3); 3.88 (dd, J=11 and 7, 1H: —H 7); 4.17 and 4.32 (2 d, J=8.5, 1H each: —CH$_2$— 20); 4.19 and 4.27 (2 d, J=15, 1H each: —OCOCH$_2$OCH$_3$); 4.65 (mt, 1H: —H 2'); 4.97 (broad d, J=10, 1H: —H 5); 5.25 (broad d, J=10, 1H: —H 3'); 5.42 (d, J=10, 1H: —CONH—); 5.66 (d, J=7, 1H: —H 2); 6.18 (broad t, J=9, 1H: —H 13); 6.52 (s, 1H: —H 10); from 7.30 to 7.50 (mt, 5H: —C$_6$H$_5$ 3'); 7.51 [(t, J=7.5, 2H: —OCOC$_6$H$_5$(—H 3 and H 5)]; 7.63 [(t, J=7.5, 1H: —OCOC$_6$H$_5$(—H 4)]; 8.12 (d, J=7.5, 2H: —OCOC$_6$H$_5$(—H 2 and H 6)].

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers. However, the compositions can also take the form of tablets, pills, powders or granules which can be administered orally.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents, for instance nitrogen mustards such as mechloretamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic response effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ethanol, and the solution is then diluted by adding 18 cm³ of physiological saline.

The composition is administered by perfusion over 1 hour by introduction in physiological solution.

We claim:
1. A taxoid of general formula:

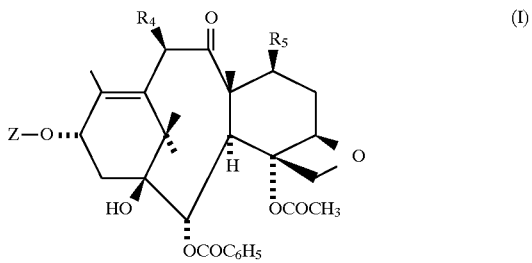

in which:
Z represents a hydrogen atom or a radical of general formula:

in which:
$R_1$ represents a benzoyl radical unsubstituted or substituted with one or more identical or different atoms or radicals selected from halogen atoms alkyl radicals containing 1 to 4 carbon atoms, alkoxy radicals containing 1 to 4 carbon atoms, and trifluoromethyl radicals, or $R_1$ represents a thenoyl radical, a furoyl radical or a radical $R_2$—O—CO— in which $R_2$ represents:
an alkyl radical containing 1 to 8 carbon atoms, and alkenyl radical containing 2 to 8 carbon atoms, an alkynyl radical containing 3 to 8 carbon atoms, a cycloalkyl radical containing 3 to 6 atoms, a cycloalkenyl radical containing 4 to 6 carbon atoms, or a bicycloalkyl radical containing 7 to 10 carbon atoms, these radicals being unsubstituted or substituted with one or more substituents selected from halogen atoms, hydroxyl radicals, alkoxy radicals containing 1 to 4 carbon atoms, dialkylamino radicals in which each alkyl portion contains 1 to 4 carbon atoms, piperidino radicals, morpholino radicals, 1-piperazinyl radicals (unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (unsubstituted or substituted with one or more atoms or radicals selected from halogen atoms, alkyl radicals containing 1 to 4 carbon atoms, and alkoxy radicals containing 1 to 4 carbon atoms), cyano radicals, carboxyl radicals, and alkoxycarbonyl radicals in which the alkyl portion contains 1 to 4 carbon atoms;
a phenyl or α- or β-naphthyl radical unsubstituted or substituted with one or more atoms or radicals selected from halogen atoms, alkyl radicals containing 1 to 4 carbon atoms, alkoxy radicals containing 1 to 4 carbon atoms, and 5-membered aromatic heterocyclic radicals;
or a saturated heterocyclic radical containing 4 to 6 carbon atoms, unsubstituted or substituted with one or more alkyl radicals containing 1 to 4 carbon atoms;
$R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical unsubstituted or substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, and trifluoromethyl radicals, and a 5-membered aromatic heterocycle containing one or more identical or different hetero atoms selected from nitrogen, oxygen and sulphur atoms and unsubstituted or substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl, and alkoxycarbonyl radicals, wherein for the substituents of the phenyl, α- or β-naphthyl and aromatic heterocyclic radicals, the alkyl radicals and the alkyl portions of the other radicals contain 1 to 4 carbon atoms, the alkenyl and alkynyl radicals contain 2 to 8 carbon atoms, and the aryl radicals are phenyl or α- or β-naphthyl radicals;

$R_4$ represents an alkanoyloxy radical in which the alkanoyl portion contains 2 to 6 carbon atoms in an unbranched or branched chain with the exception of an acetyl radical, an alkenoyloxy radical in which the alkenoyl portion contains 3 to 6 carbon atoms in an unbranched or branched chain, or an alkynoyloxy radical in which the alkynoyl portion contains 3 to 6 carbon atoms in an unbranched or branched chain, these radicals being unsubstituted or substituted with one or more halogen atoms, an alkoxy radical containing 1 to 4 carbon atoms, an alkylthio radical containing 1 to 4 carbon atoms, a carboxyl radical, an alkyloxycarbonyl radical in which the alkyl portion contains 1 to 4 carbon atoms, a cyano radical, a carbamoyl radical in which each alkyl portion contains 1 to 4 carbon atoms or, with the nitrogen atom to which it is linked, forms a saturated 5- or 6-membered heterocyclic radical which may contain a second hetero atom selected from oxygen, sulphur or nitrogen atoms, unsubstituted or substituted with an alkyl radical containing 1 to 4 carbon atoms, a phenyl radical, or a phenylalkyl radical in which the alkyl portion contains 1 to 4 carbon atoms, or alternatively $R_4$ represents a cycloalkanoyloxy radical in which the cycloalkanoyl portion contains 4 to 8 carbon atoms or a cycloalkenoyloxy radical in which the cycloalkenoyl portion contains 4 to 8 carbon atoms, or alternatively $R_4$ represents a benzoyloxy radical or a heterocyclic carbonyloxy radical in which the heterocyclic portion represents a 5- or 6-membered aromatic heterocycle containing one or more hetero atoms selected from oxygen, sulphur and nitrogen atoms;

$R_5$ represents an alkoxy radical containing 1 to 6 atoms in an unbranched or branched chain, unsubstituted or substituted with an alkoxy radical containing 1 to 4 carbon atoms, an alkenyloxy radical containing 3 to 6 carbon atoms, an alkynyloxy radical containing 3 to 6 carbon atoms, a cycloalkyloxy radical containing 3 to 6 carbon atoms, or a cycloalkenyloxy radical containing 3 to 6 carbon atoms, these radicals unsubstituted or substituted with one or more halogen atoms, an alkoxy radical containing 1 to 4 carbon atoms, an alkylthio radical containing 1 to 4 carbon atoms, a carboxyl radical, an alkyloxycarbonyl radical in which the alkyl portion contains 1 to 4 carbon atoms, a cyano radical, a carbamoyl radical, an N-alkylcarbamoyl radical, or an N,N-dialkylcarbamoyl radical in which each alkyl portion contains 1 to 4 carbon atoms or, with the nitrogen atom to which it is linked, forms a saturated 5- or 6-membered heterocyclic radical which may contain a second hetero atom selected from oxygen, sulphur and nitrogen atoms, unsubstituted or substituted with an alkyl radical containing 1 to 4 carbon atoms, a phenyl radical, or a phenylalkyl radical in which the alkyl portion contains 1 to 4 carbon atoms.

2. A taxoid according to claim 1 in which Z represents a hydrogen atom or a radical of general formula (II) in which:

$R_1$ represents a benzoyl radical or a radical $R_2$—O—CO— in which $R_2$ represents a tert-butyl radical;

$R_3$ represents an alkyl radical containing 1 to 6 carbon atoms, an alkenyl radical containing 2 to 6 carbon atoms, a cycloalkyl radical containing 3 to 6 atoms, a phenyl radical unsubstituted or substituted with one or more identical or different atoms or radicals selected from halogen atoms, alkyl, alkoxy, dialkylamino, acylamino, alkoxycarbonylamino, trifluoromethyl, 2- or 3-furyl, 2- or 3-thienyl, and 2-, 4- or 5-thiazolyl radicals;

$R_4$ represents an alkyloxyacetoxy radical in which the alkyl portion contains 1 to 4 carbon atoms, a cycloalkanoyloxy radical in which the cycloalkanoyl portion contains 4 to 8 carbon atoms, or a pyridylcarbonyloxy radical; and $R_5$ represents an unbranched or branched alkyloxy radical containing 1 to 6 carbon atoms.

3. A taxoid according to claim 1 for which Z represents a hydrogen atom or a radical of general formula (II) in which $R_1$ represents a benzoyl radical or a radical $R_2$—O—CO— in which $R_2$ represents a tert-butyl radical, $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, $R_4$ represents a methoxyacetoxy, cyclopropylcarbonyloxy, cyclopentylcarbonyloxy, 2-pyridylcarbonyloxy or 3-pyridylcarbonyloxy radical, and $R_5$ represents a methoxy radical.

4. A process for preparing the taxoid according to claim 1 in which Z represents a radical of general formula (II), comprising esterifying a product of general formula:

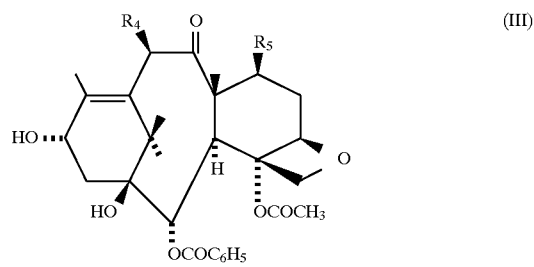

in which $R_4$ and $R_5$ are defined as in claim 1 by means of an acid of general formula:

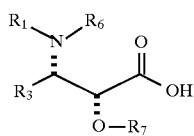
(IV)

in which $R_1$ and $R_3$ are defined as in claim 1, and either $R_6$ represents a hydrogen atom and $R_7$ represents a group protecting the hydroxyl function, or $R_6$ and $R_7$ together form a saturated 5- or 6-membered heterocycle, or by means of a derivative of this acid, to obtain an ester of general formula:

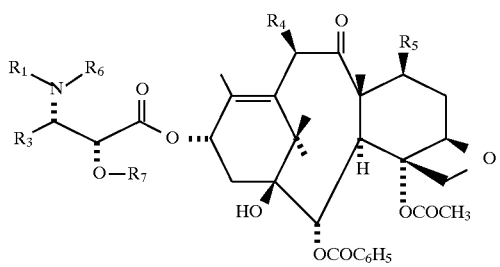
(V)

in which $R_1$, $R_3$, $R_4$, $R_5$, $R6$ and $R_7$ are defined as above, followed by replacing the protective groups represented by either one or both of $R_7$ or $R_6$ and $R_7$, with hydrogen atoms.

5. The process according to claim 4, wherein the esterification is performed by means of an acid of general formula (IV) in the presence of a condensing agent and an activating agent in an organic solvent at a temperature between −10° and 90° C.

6. The process according to claim 4, wherein the esterification is performed by means of an acid of general formula (IV) in the form of the symmetrical anhydride, working in the presence of an activating agent in an organic solvent at a temperature between 0° and 90° C.

7. The process according to claim 4, wherein the esterification is performed using the acid of general formula (IV) in halide form or in the form of a mixed anhydride with an aliphatic or aromatic acid, which may be prepared in situ, in the presence of a base, working in an organic solvent at a temperature between 0° and 80° C.

8. The process according to claim 4, wherein either one or both of the protective groups $R_7$ or $R_6$ and $R_7$ are replaced by hydrogen atoms in the following manner:

1) when $R_6$ represents a hydrogen atom and $R_7$ represents a group protecting the hydroxyl function, the protective groups a re replaced by hydrogen atoms by means of an inorganic or organic acid used alone or mixed, working in an organic solvent selected from alcohols, ethers, esters, aliphatic hydrocarbons, halogenated aliphatic hydrocarbons, aromatic hydrocarbons, or nitriles at a temperature between −10° and 60° C.;

2) when $R_6$ and $R_7$ together form a saturated 5- or 6-membered heterocycle of general formula:

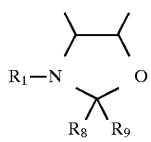
(VI)

in which $R_1$ is defined as above and $R_8$ and $R_9$, which may be identical or different, represent a hydrogen atom, an alkyl radical containing 1 to 4 carbon atoms, an aralkyl radical in which the alkyl portion contains 1 to 4 carbon atoms, or an aryl radical, or alternatively $R_8$ represents an alkoxy radical containing 1 to 4 carbon atoms, a trihalomethyl radical, or a phenyl radical substituted with a trihalomethyl radical and $R_9$ represents a hydrogen atom, or alternatively $R_8$ and $R_9$, together with the carbon atom to which they are linked, form a 4- to 7-membered ring; the protective group formed by $R_6$ and $R_7$ is replaced by hydrogen atoms in the following manner:

a) when $R_1$ represents a tert-butoxycarbonyl radical and $R_8$ and $R_9$, which may be identical or different, represent an alkyl, aralkyl, or aryl radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, the ester of general formula (V) is treated with an inorganic or organic acid, where appropriate in an organic solvent, to obtain the product of general formula:

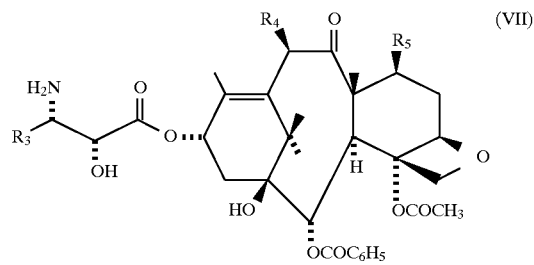
(VII)

in which $R_3$, $R_4$ and $R_5$ are defined as above, which product of formula VII is acylated by means of benzoyl chloride in which the phenyl ring is unsubstituted or substituted or acylated by means of thenoyl chloride, furoyl chloride, or a product of general formula:

$$R_2-O-CO-X \qquad (VIII)$$

in which $R_2$ is defined as above and X represents a halogen atom or a residue $-O-R_2$ or $-O-CO-O-R_2$, to obtain a product of general formula (I) in which Z represents a radical of general formula (II);

b) when $R_1$ represents an unsubstituted or substituted benzoyl radical, thenoyl radical, or furoyl radical, or a radical $R_2-O-CO$ in which $R_2$ is defined as above, $R_8$ represents a hydrogen atom, an alkoxy radical containing 1 to 4 carbon atoms, or a phenyl radical substituted with one or more alkoxy radicals containing 1 to 4 carbon atoms and $R_9$ represents a hydrogen atom; the protective group formed by $R_6$ and $R_7$ is replaced by hydrogen atoms in the presence of an inorganic acid used alone or mixed in a stoichiometric or catalytic amount, working in an organic solvent selected from alcohols, ethers, esters, aliphatic hydrocarbons, halogenated aliphatic hydrocarbons, and aromatic hydrocarbons at a temperature between −10° to 60° C.

9. A process for preparing a taxoid according to claim 1 for which Z represents a hydrogen atom, $R_4$ and $R_5$ are defined as in claim 1, comprising treating a 10-deacetylbaccatin III of formula:

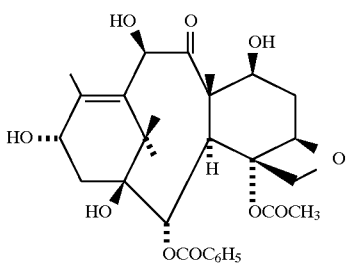

(IX)

with a silyl halide of general formula:

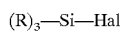 (X)

in which the symbols R, which may be identical or different, represent an alkyl radical containing 1 to 4 carbon atoms, unsubstituted or substituted with a phenyl radical, a cycloalkyl radical containing 3 to 6 carbon atoms, or a phenyl radical, to obtain a product of general formula:

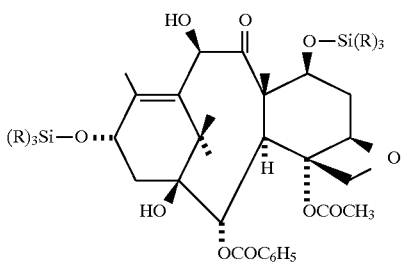

(XI)

defined as above, which product of formula (XI) is treated with a product of general formula:

$R'_4$—$X_1$ (XII)

in which $R'_4$ is such that $R'_4$—O— is identical to $R_4$ defined above and $X_1$ represents a halogen atom, to obtain a product of general formula:

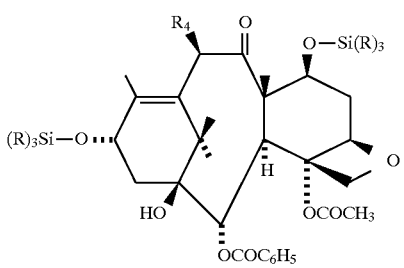

(XIII)

in which R and $R_4$ are defined as above, the silyl protective groups of which are replaced by hydrogen atoms to obtain a product of general formula:

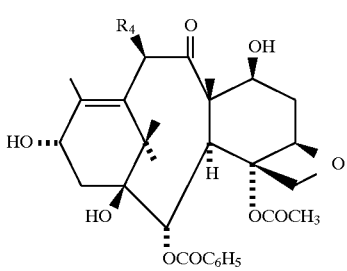

(XIV)

in which $R_4$ is defined as above, which is etherified selectively at position 7 by the action of a product of general formula:

 (XV)

in which $R'_5$ is such that $R'_5$—O— is identical to $R_5$ defined above and $X_2$ represents a reactive ester residue or a halogen atom, to give the product of general formula (I) in which Z represents a hydrogen atom.

10. A process for preparing a taxoid according to claim 1 in which Z represents a radical of general formula (II), $R_4$ and $R_5$ are defined as in claim 1, comprising treating a product of general formula:

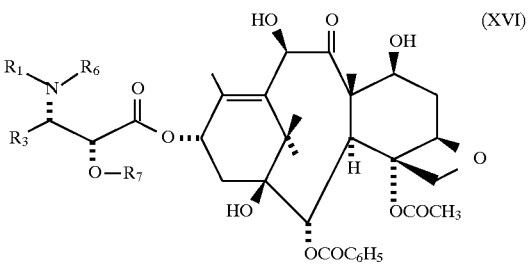

(XVI)

in which $R_1$, $R_3$, $R_6$ and $R_7$ are defined as in claim 1 by means of a product of general formula:

$(R)_3Si$—Hal (X)

in which the symbols R, which may be identical or different, represent an alkyl radical containing 1 to 4 carbon atoms unsubstituted or substituted with a phenyl radical, a cycloalkyl radical containing 3 to 6 carbon atoms, or a phenyl radical, to obtain a product of general formula:

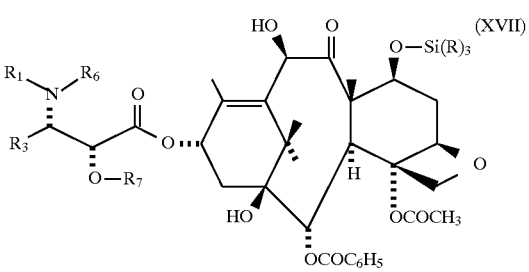

(XVII)

in which R, $R_1$, $R_3$, $R_6$ and $R_7$ are defined as above, which is reacted with a product of general formula:

$R'_4$—$X_1$ (XII)

in which $R_4$ is such that $R'_4$—O— is identical to $R_4$ defined as in claim 1 and $X_1$ represents a halogen atom or a reactive ester residue, to give a product of general formula:

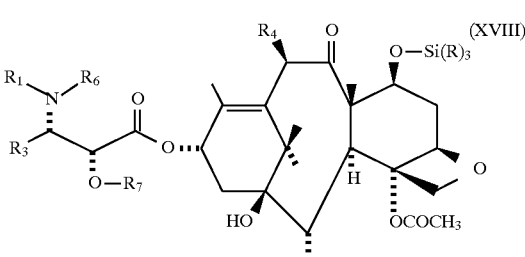

(XVIII)

in which R, $R_1$, $R_3$, $R_4$, $R_6$ and $R_7$ are defined as above, the silyl protective group of which is replaced by a hydrogen atom to give a product of general formula:

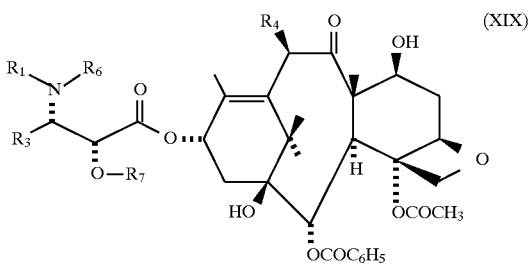

wherein $R_1$, $R_3$, $R_4$, $R_6$ snd $R_7$ are defined as above, which, by the action of a product of general formula (XV), yields the product of general formula (V):

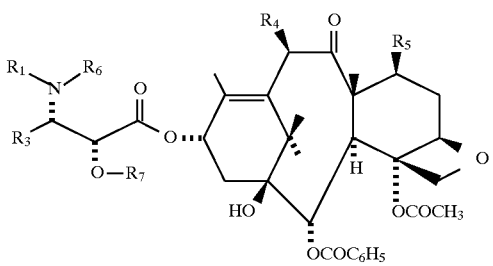

the protective groups of which are replaced by hydrogen atoms to give a product of general formula (I) in which Z represents a radical of general formula (II).

11. A process of preparing a taxoid according to claim 1, comprising reacting activated Raney nickel, in the presence of an aliphatic alcohol containing 1 to 3 carbon atoms or an ether, with a product of general formula:

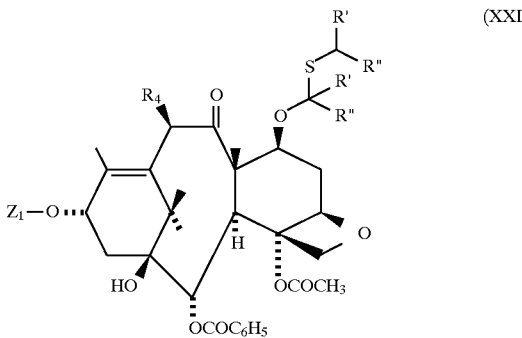

in which $R_4$ is defined as in claim 1 and R' and R", which may be identical or different, represent a hydrogen atom, an alkyl radical containing 1 to 6 carbon atoms, an alkenyl radical containing 2 to 6 carbon atoms, an alkynl radical containing 3 to 6 carbon atoms, a cycloalkyl radical containing 2 to 6 carbon atoms, or a cycloalkenyl radical containing 3 to 6 carbon atoms, unsubstituted or substituted, or alternatively R' and R", together with the carbon atom to which they are linked, form a cycloalkyl radical containing 3 to 6 carbon atoms or a cycloalkenyl radical containing 4 to 6 carbon atoms, and $Z_1$ represents a hydrogen atom or a radical of general formula:

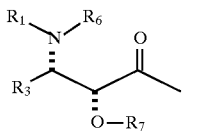

in which $R_1$ and $R_3$ are defined as in claim 1 and $R_6$ and $R_7$ are defined as in claim 4, to obtain a product of general formula:

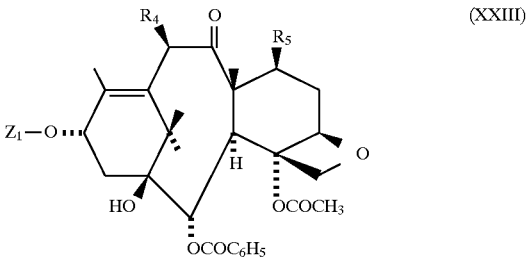

in which $R_4$ and $R_5$ are defined as above, followed, when $Z_1$ represents a radical of general formula (XXII), by replacement of the protective groups represented by either or both of $R_6$ or $R_6$ and $R_7$ by hydrogen atoms under the conditions of claim 8.

12. The process according to claim 11, performed at a temperature between −10° and 60° C.

13. 4α-Acetoxy-2α-benzoyloxy-5β,20-epoxy-1β-hydroxy-7β-methoxy-10β-methoxyacetoxy-9-oxo-11-taxen-13α-yl (2R,3S)-3-tert-butoxycarbonylamino-2-hydroxy-3-phenylpropionate.

14. 4α-Acetoxy-2α-benzoyloxy-1β-hydroxy-5β,20-epoxy-7β-methoxy-10β-cyclopropylcarbonyloxy-9-oxo-11-taxen-13α-yl (2R,3S)-3-tert-butoxycarbonylamino-2-hydroxy-3-phenylpropionate.

15. 4α-Acetoxy-2α-benzoyloxy-1β-hydroxy-5β,20-epoxy-7β-methoxy-10β-cyclopentylcarbonyloxy-9-oxo-11-taxen-13α-yl (2R,3S)-3-tert-butoxycarbonylamino-2-hydroxy-3-phenylpropionate.

16. 4α-Acetoxy-2α-benzoyloxy-1β-hydroxy-5β,20-epoxy-7β-methoxy-10β-(2-pyridyl)carbonyloxy-9-oxo-11-taxen-13α-yl (2R,3S)-3-tert-butoxycarbonylamino-2-hydroxy-3-phenylpropionate.

17. 4α-Acetoxy-2α-benzoyloxy-1β-hydroxy-5β,20-epoxy-7β-methoxy-10β-(3-pyridyl)carbonyloxy-9-oxo-11-taxen-13α-yl (2R,3S)-3-tert-butoxycarbonylamino-2-hydroxy-3-phenylpropionate.

18. A pharmaceutical composition comprising at least one taxoid according to claim 1 in which Z represents a radical of general formula (II), and one or more pharmaceutically acceptable carriers.

19. A pharmaceutical composition comprising the compound of claim 13 and one or more pharmaceutically acceptable carriers.

20. A pharmaceutical composition comprising the compound of claim 14 and one or more pharmaceutically acceptable carriers.

21. A pharmaceutical composition comprising the compound of claim 15 and one or more pharmaceutically acceptable carriers.

22. A pharmaceutical composition comprising the compound of claim 16 and one or more pharmaceutically acceptable carriers.

23. A pharmaceutical composition comprising the compound of claim 17 and one or more pharmaceutically acceptable carriers.

24. The taxoid according to claim 1, wherein the $R_2$ 5-membered aromatic heterocyclic radical substituent is a furyl or thienyl radical.

25. The method of claim 8, wherein the aryl portion of either or both of the $R_8$ or $R_9$ aralkyl radicals is a phenyl radical unsubstituted or substituted with one or more alkoxy radicals containing 1 to 4 carbon atoms.

26. The method of claim 8, wherein either or both or the $R_8$ or $R_9$ aryl radicals is a phenyl radical unsubstituted or substituted with one or more alkoxy radicals containing 1 to 4 carbon atoms.

27. The process of claim 8, wherein the trihalomethyl radical is a trichloromethyl radical.

28. The process of claim 8, wherein the organic solvent is an alcohol.

29. The pharmaceutical composition of one of claims 18 to 23, wherein the pharmaceutically acceptable carrier is a diluent or adjuvant.

30. The pharmaceutical composition of one of claims 18 to 23, further comprising another pharmacologically active compound.

* * * * *

UNITED STATES PATENT AND TRADEMARK OFFICE
CERTIFICATE OF CORRECTION

PATENT NO. : 5,889,043
DATED : March 30, 1999
INVENTOR(S) : Herve BOUCHARD et al.

It is certified that error appears in the above-identified patent and that said Letters Patent is hereby corrected as shown below:

On the Title Page, Item [75], in the Inventors, line 1, "Thiaia" should read --Thiais--.
In Claim 1, col. 22, line 25, after "atoms", insert --,--.
In Claim 1, col. 22, line 29, after "radical" (first occurrence), insert --,--.
In Claim 4, col. 25, line 23, "R6" should read --$R_6$--.
In Claim 8, col. 25, line 47, "a re" should read --are--.
In Claim 9, col. 27, line 31, before "defined", insert --in which R is--.
In Claim 10, col. 29, line 13, "$R_6$snd" should read --$R_6$, and--.
In Claim 26, col. 31, line 1, "or both or" should read --or both of--.

Signed and Sealed this

Twenty-third Day of May, 2000

Attest:

Q. TODD DICKINSON

*Attesting Officer*        *Director of Patents and Trademarks*